(12) United States Patent
Vogt et al.

(10) Patent No.: US 10,507,261 B2
(45) Date of Patent: Dec. 17, 2019

(54) PASTY TWO-COMPONENT POLYMETHACRYLATE BONE CEMENT

(71) Applicant: HERAEUS MEDICAL GMBH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 15/615,209

(22) Filed: Jun. 6, 2017

(65) Prior Publication Data

US 2017/0348457 A1    Dec. 7, 2017

(30) Foreign Application Priority Data

Jun. 7, 2016    (DE) .................. 10 2016 209 988

(51) Int. Cl.
| | | |
|---|---|---|
| *A61L 24/02* | (2006.01) | |
| *A61L 24/06* | (2006.01) | |
| *C08L 33/12* | (2006.01) | |
| *A61L 24/00* | (2006.01) | |
| *A61L 24/04* | (2006.01) | |
| *A61L 27/16* | (2006.01) | |
| *C08F 265/06* | (2006.01) | |

(52) U.S. Cl.
CPC ......... *A61L 24/0021* (2013.01); *A61L 24/043* (2013.01); *A61L 24/06* (2013.01); *A61L 27/16* (2013.01); *C08F 265/06* (2013.01); *A61L 24/001* (2013.01); *A61L 2430/02* (2013.01)

(58) Field of Classification Search
CPC ......... A61L 27/16; A61L 24/043; C08L 33/12
See application file for complete search history.

(56) References Cited

U.S. PATENT DOCUMENTS

| | | | |
|---|---|---|---|
| 3,520,825 A | 7/1970 | Koehler et al. | |
| 4,268,639 A * | 5/1981 | Seidel .................... | A61L 24/06 525/303 |
| 4,588,583 A | 5/1986 | Pietsch et al. | |
| 8,536,243 B2 | 9/2013 | Leonard et al. | |
| 8,829,073 B2 | 9/2014 | Nies | |
| 9,387,275 B2 | 7/2016 | Vogt et al. | |
| 9,457,110 B2 | 10/2016 | Vogt | |
| 2007/0031469 A1 * | 2/2007 | Kuhn .................... | A61L 24/001 424/423 |
| 2009/0105144 A1 | 4/2009 | Vogt et al. | |
| 2009/0105366 A1 | 4/2009 | Vogt et al. | |
| 2011/0054392 A1 | 3/2011 | Nies | |
| 2011/0237705 A1 | 9/2011 | Leonard et al. | |
| 2011/0270259 A1 | 11/2011 | Shim | |
| 2012/0265209 A1 * | 10/2012 | Druma ................ | B01F 11/0054 606/93 |
| 2012/0289608 A1 | 11/2012 | Sattig et al. | |
| 2013/0125786 A1 | 5/2013 | Vogt | |
| 2013/0310466 A1 | 11/2013 | Vogt | |
| 2015/0051305 A1 | 2/2015 | Sattig et al. | |
| 2016/0243274 A1 | 8/2016 | Chisholm et al. | |
| 2016/0346426 A1 | 12/2016 | Vogt | |

FOREIGN PATENT DOCUMENTS

| | | |
|---|---|---|
| CA | 2 682 140 A1 | 10/2008 |
| CA | 2 867 934 A1 | 10/2013 |
| DE | 1 567 481 A1 | 10/1970 |
| DE | 32 45 956 A1 | 6/1984 |
| DE | 10 2007 015 698 | 10/2008 |
| DE | 10 2007 052 116 A1 | 4/2009 |
| DE | 10 2007 050 762 B3 | 5/2009 |
| DE | 10 2008 030 312 A1 | 1/2010 |
| DE | 10 2009 043 550 A1 | 5/2011 |
| EP | 2 664249 A1 | 11/2013 |
| EP | 2 596 812 B1 | 6/2015 |
| WO | 2015 044689 A1 | 4/2015 |

OTHER PUBLICATIONS

Kühn, "Bone Cements: Up-to-date Comparison of Physical and Chemical Properties of Commercial Materials", Springer-Verlag Berlin Heidelberg New York, 2000.
German Office Action issued in corresponding application dated Jan. 27, 2017.
European Search Report in corresponding application Ep 17162233 dated Sep. 1, 2017.

\* cited by examiner

*Primary Examiner* — Tae H Yoon
(74) *Attorney, Agent, or Firm* — Norris McLaughlin, P.A.

(57) ABSTRACT

A pasty two-component polymethacrylate bone cement comprising a pasty component A, containing
AI at least one distillable methacrylate monomer for radical polymerisation;
AII at least one polymer soluble in AI;
AIII at least one particulate polymer with a particle size of no more than 500 μm that is not soluble in AI;
AIV at least one radical stabiliser; and
AV at least one aromatic amine accelerator;
and a pasty component B, containing
BI dibenzoyl peroxide;
BII at least one substance that is not subject to radical polymerisation and is liquid at room temperature, whereby the solubility of dibenzoyl peroxide in this substance at room temperature is less than 5.0% by weight and, whereby the weight fraction of liquid substance BII in the self-curing cement dough is less than 2.0% by weight. Also disclosed is a method for producing a self-curing bone cement dough using the pasty two-component polymethacrylate bone cement.

21 Claims, No Drawings

PASTY TWO-COMPONENT POLYMETHACRYLATE BONE CEMENT

This application claims priority of German Patent Application No. DE 10 2016 209 988.4, filed Jun. 7, 2016, the entire contents of which are incorporated herein by reference.

The subject matter of the invention is a pasty two-component polymethacrylate bone cement. Moreover, a method for producing a self-curing bone cement dough and the use of the pasty two-component polymethacrylate bone cement are subject matters of the invention.

Polymethacrylate bone cements have been in use in medicine for decades for permanent mechanical fixation of total joint endoprostheses. These are based on powder-liquid systems, whereby it is customary to use methylmethacrylate as monomer. A general overview is provided, e.g., in K.-D. Kühn, "Bone Cements: Up-to-date Comparison of Physical and Chemical Properties of Commercial Materials", Springer-Verlag Berlin Heidelberg New York, 2000.

Aside from the powder-liquid cements, polymethylmethacrylate bone cements based on the use of cement pastes have also been proposed.

DE 10 2007 052116 A1 relates to a one-component bone cement. DE 32 45 956 A1, DE 10 2007 050762 B3, and DE 10 2008 030312 A1 describe two-component bone cements made of two cement pastes that are stored separately in suitable cartridges. Said pastes always contain one methacrylate monomer and at least one polymer dissolved therein. Moreover, said pastes can also contain cross-linked polymer particles that are insoluble in the methacrylate monomer. Both pasty components separately contain components of a redox initiator system that react only after the two pasty components are mixed and, in the process, form radicals, which initiate the radical polymerisation of the methacrylate monomer that leads to the curing of the mixed cement dough. Redox initiator systems based on thermally stable hydroperoxides are particularly well-suited. EP 2 664 349 B1 describes a paste cement with a redox initiator system that is based on the use of hydroperoxides.

Proven for decades, the dibenzoyl peroxide/N—N-p-toluidine redox initiator system is suitable for pasty two-component polymethacrylate bone cements only to a limited degree, since the dibenzoyl peroxide dissolved in the liquid monomer always shows a low degree of spontaneous degradation that limits the storage time of the cement pastes. In the solid, undissolved aggregate state, dibenzoyl peroxide is clearly more stable during storage than in the dissolved state.

U.S. Pat. No. 8,536,243 B2 describes a powder-gel bone cement system. This is a modification of the conventional powder-liquid bone cements. The powdered component consists of a polymer, an initiator such as dibenzoyl peroxide, and, if applicable, a radiopaquer, and hydroxyl apatite. The gel-like component comprises an acrylic monomer such as methylmethacrylate, a radical inhibitor such as hydroquinone, an activator such as N,N-dimethyl-p-toluidine, and a polymer that is dissolved in the acrylic monomer and has a mean molecular weight above 1,000,000 g/mol. The dibenzoyl peroxide is present as a solid in the cement powder of this cement.

An analogous bone cement system is disclosed in US 2011 270 259 A1.

DE 10 2007 015698 B4 describes an implant material. Said implant material consists of a paste that is stable during storage and a monomer liquid that is stored separately. The paste that is stable during storage is a mixture of at least one particulate polymer, a starter component for radical polymerisation, and a carrier liquid, in which the particulate polymer is not soluble and which does not swell, and in which the starter component is insoluble. Relatively large weight fractions of carrier liquid are necessary in order to wet all of the cement powder and transfer it into a pasty state. Methylmethacrylate or other esters of methacrylic acid are proposed as separate monomer liquid. Dibenzoyl peroxide is used as starter component. The compressive strength of the cured implant material is relatively low and is below the requirements of ISO 5833 for the compressive strength being more than or equal to 70 MPa, as is illustrated by example 3 of DE 10 2007 015698 A1. Presumably, the underlying reason is that the carrier liquid is not miscible with the monomer liquid and does not partake in the radical polymerisation either. In this case, a porous implant material possessing only low mechanical strength is generated. Accordingly, the use of this implant material is hardly suitable for load-bearing permanent anchoring of articular endoprostheses.

It is the object of the invention to develop a pasty two-component polymethacrylate bone cement that contains dibenzoyl peroxide as initiator. Said bone cement is to be made up of two pasty components A and B, whereby pasty component A contains an accelerator and pasty component B contains the initiator and and has an appropriate composition such that it is stable during storage at room temperature. It is important for pasty component B to be present as a mass that is flowable mass when exposed to pressure and is suitable for being filled into cartridges by means of conventional paste filling machines.

It is another object of the invention to provide a pasty two-component polymethacrylate bone cement, whose cured cement dough, after the mixing of the two pasty cement components is completed, meets the requirements of ISO 5833, i.e. the compressive strength is more than or equal to 70 MPa, the flexural strength is more than or equal to 50 MPa, and the flexural modulus is more than or equal to 1800 MPa.

The object of the invention is met by a pasty two-component polymethacrylate bone cement as described hereinbelow.

According to the invention, a pasty two-component polymethacrylate bone cement comprises a pasty component A and a pasty component B. Pasty component A contains AI at least one distillable methacrylate monomer for radical polymerisation, AII at least one polymer that is soluble in AI, AIII at least one particulate polymer with a particle size of no more than 500 µm that is not soluble in AI, AIV at least one radical stabiliser, and AV at least one accelerator from the group of aromatic amines. Pasty component B contains BI dibenzoyl peroxide, BII at least one substance that is not subject to radical polymerisation and is liquid at room temperature, whereby the solubility of dibenzoyl peroxide in this substance at room temperature is less than 5.0% by weight. In this context, the weight fraction of liquid substance BII in the self-curing cement dough thus formed after the mixing of pasty component A with pasty component B is completed is less than 2.0% by weight.

Where an embodiment is described herein as "comprising," the present invention separately also contemplates the analogous embodiments "containing," "consisting of," or "consisting essentially of." Likewise, where an embodiment is described herein as "containing," the present invention separately also contemplates the analogous embodiments "consisting of" or "consisting essentially of."

The particle size D50 shall be understood to be the volume average of the particle size. D50 is determined by means of a laser diffraction method using scattered light and the laser diffraction particle size analyzer LS 13320 made by Beckman Coulter, USA.

The number average molar mass is determined by means of gel permeation chromatography (GPC).

In the scope of the present invention, the term "methacrylate" shall be understood to mean alkyl ester of methacrylic acid. Esters of mono- and divalent alcohols with 1 to 4 carbon atoms are preferred. Pertinent examples are methylmethacrylate and ethylene glycol methacrylate.

The term "polymethacrylate" shall be understood to mean polymer of an alkyl ester of methacrylic acid. Polymers of the methyl and ethyl ester are preferred, i.e. polymethyl methacrylate and polyethyl methacrylate, in particular polymethyl methacrylate.

The term, "soluble in methacrylate", shall be understood to mean that a solution that is clear to the eye is formed. This is determined visually by eye.

Referring to the methacrylate-insoluble particulate polymer that has a particle size D50 of at most 500 μm, the term, "insoluble in methacrylate", shall be understood to mean that no solution that is clear to the eye is formed. This is determined visually by eye.

The invention is based on finding, surprisingly and in contrast to the bone cement described in DE 10 2007 015698 B4, that pasty component B can be prepared from dibenzoyl peroxide and a substance, which is not subject to radical polymerisation and is liquid at room temperature and in which the solubility of dibenzoyl peroxide at room temperature is less than 5.0% by weight, without requiring polymeric particles or polymers that are dissolved in a solvent to allow for the formation of a paste. What is surprising in this context is that said paste can be plastically deformed without any difficulty and can be processed in the same manner as pastes that contain dissolved or suspended polymers. Said paste can be mixed without any difficulty with pastes that contain methacrylate monomers, in which dibenzoyl peroxide is soluble. It was evident, surprisingly, that pasty component B and pasty component A are very easy to mix, which is in contrast to the mixing of two pasty components, which both contain dissolved polymers.

It was also evident, surprisingly, that the mixing of pasty components A and B of the two-component polymethacrylate bone cement according to the invention allow us a cement dough to be obtained that meets the requirements of ISO 5833 with regard to a compressive strength of more than or equal to 70 MPa, a flexural strength of more than or equal to 50 MPa, and a flexural modulus of more than or equal to 1800 MPa once it is cured.

Pasty components A and B can be stored in cartridges made of plastic material or in coated metal cartridges, in particular lacquered aluminium cartridges. The mixing of pasty components A and B to form a tack-free cement dough can be effected with a static mixer that is arranged in a dispensing tube connected to the cartridges on the cartridge head. The cartridges can be present as coaxial cartridges, as side-by-side cartridges or as individual cartridges that are not connected to each other, in which pasty components A and B are stored separately prior to mixing.

The paste used as component A comprises AI at least one distillable monomer for radical polymerisation. Examples of said monomers are, in particular, methacrylic acid esters. Methylmethacrylate and ethylene glycol dimethacrylate are preferred as methacrylate monomer.

Methylmethacrylate is particularly preferred as distillable monomer for radical polymerisation. The weight fraction of the monomer in component A can vary in broad ranges, whereby the weight fraction preferably is in the range of 10 to 70 wt. %. Preferably, the weight fraction of MMA in component A is in the range of 30 to 50 wt. %.

The paste used as component A further comprises AII at least one polymer that is soluble in the distillable monomer for radical polymerisation. As a matter of principle, all methylmethacrylate-soluble polymers can be used. One or more methylmethacrylate-soluble polymers can be used. Examples of suitable polymers include polymethylmethacrylate and copolymers of methylmethacrylate and one or more monomers that can be copolymerised with it, such as methylacrylate, styrene, and ethylacrylate. Polymethylmethacrylate, poly-methylmethacrylate-copolymers or mixtures thereof are preferred as polymer AII, whereby polymethylmethacrylate-co-methylacrylate or polymethylmethacrylate-co-styrene are particularly preferred as polymer.

Preferably, the soluble polymer has a number average molar mass of less than 500,000 Dalton. The number average molar mass of the at least one methacrylate-soluble polymer preferably is at least 100,000 Dalton.

The weight fraction of the at least one methacrylate-soluble polymer in component A can vary in broad ranges. It can, for example, be in the range of 15 to 45 wt. %, whereby the weight fraction preferably is in the range of 25 to 35 wt. %.

The paste used as component A further comprises at least one methacrylate-insoluble particulate polymer. Preferably, the methacrylate-insoluble particulate polymer has a density that differs only little from the density of methacrylate. As a result, there is little or virtually no sedimentation of insoluble polymer particles in paste A evident.

On principle, all polymers that are insoluble in methacrylate can be used as methacrylate-insoluble polymer particles. Examples of suitable polymers include cross-linked polymethylmethacrylate, cross-linked poly(methylmethacrylate-co-methacrylate), and cross-linked poly(methylmethacrylate-co-styrene).

Cross-linked polymethylmethacrylate and cross-linked poly(methylmethacrylate-co-methacrylate) are a copolymer of methylmethacrylate or a mixture of methylmethacrylate and methacrylate and one or more bifunctional, trifunctional and/or multi-functional monomers that can be copolymerised with it. Pertinent examples of said bifunctional, trifunctional and/or multi-functional monomers acting as cross-linkers include dimethacrylates, trimethacrylates, tetramethacrylates, diacrylates, triacrylates, tetraacrylates, whereby dimethacrylates are preferred.

Preferably, the methacrylate-insoluble particulate polymer is selected from the group consisting of cross-linked polymethylmethacrylate and cross-linked copolymers of methylmethacrylate. The methacrylate-insoluble particulate polymer AIII is particularly preferably selected from cross-linked polymethylmethacrylate and cross-linked polymethyl methacrylate-co-methyl acrylate.

The weight fraction of AIII the at least one methacrylate-soluble particulate polymer in component A can vary in broad ranges. It can, for example, be in the range of 15 to 45 wt. %, whereby the weight fraction preferably is in the range of 25 to 35 wt. %.

It is particularly preferred according to the invention to have 30-50 parts by weight (AII, 25-35 parts by weight (AII), and 25-35 parts by weight (AIII) present in pasty component A.

Particularly preferably, the weight ratio of pasty component A and pasty component B is more than or equal to 96 to 4, particularly preferably the weight ratio of component A and component B is between 94:6 and 99.9 to 0.1.

Pasty component A is stored in cartridges in the absence of atmospheric oxygen. It contains AIV a radical stabiliser. Said radical stabiliser is preferably selected from the group consisting of p-benzoquinone (CAS no. 106-51-4), o-benzoquinone (CAS no. 583-63-1), hydroquinone (CAS no. 123-31-9), 2,5-di-t-butylhydroquinone (CAS no. 88-58-4), phenothiazine (CAS no. 92-84-2) and the derivatives thereof. Preferably, the fraction of stabiliser present in component A is 0.01 to 1 wt. %.

Component A further contains AV at least one accelerator from the group of aromatic amines. Preferably, the amine is a toluidine. In this context, the accelerator AV is particularly preferably selected from the group consisting of N,N-dimethyl-p-toluidine, N,N-bis-hydroxyethyl-p-toluidine and N,N-dimethyl-p-hydroxyethyl-aniline. Preferably, the content of the accelerator in component A ranges from 0.1 wt. % to 4 wt. %.

Advantageously, one or more optional additional substances can be contained in component A, e.g. one or more colouring substances and/or one or more pharmaceutical agents.

The pharmaceutical agents in pasty component A can be selected from the groups of antibiotics, hormones, growth factors, and antiphlogistic agents. Said pharmaceutical agents can be either soluble or insoluble in monomer AI. Antibiotics such as gentamicin sulfate, tobramycin sulfate, clindamycin hydrochloride, vancomycin hydrochloride, trometamol-fosfomycin, and daptomycin are preferred as pharmaceutical agents in this context.

Paste A can further contain one or more radiopaquers, which are also referred to as X-ray contrast agents. It is customary to use radiopaquers in bone cements and they are commercially available.

The radiopaquer can be, e.g., metal oxides, e.g. zirconium dioxide, barium sulfate, toxicologically non-objectionable heavy metal particles, e.g. tantalum, ferrite, and magnetite, or toxicologically non-objectionable calcium salts, e.g. $CaCO_3$, $CaSO_4$ or $CaSO_4$ $2H_2O$.

Preferably, the radiopaquer is selected from the group consisting of zirconium dioxide, barium sulfate, tantalum, and biocompatible calcium salts.

Moreover, component A can contain, as excipients, methacrylate-soluble colourants, methacrylate-insoluble colour pigments, pyrogenic silicon dioxide, and methacrylic amide. Food colourant E141 (chlorophyllin) is particularly well-suited as methylacrylate-soluble colourant.

Water, glycerol (CAS no. 56-81-5), diglycerol (CAS no. 627-82-7), glycerol-tri-octoate (CAS nor. 528-23-8), glycerol-tri-decanoate (CAS no. 621-71-6), polyethylene glycol (CAS no. 25322-68-3), sebacic acid dibutylester (CAS no. 109-43-39) and mixtures thereof are preferred as liquid substance BII that is not subject to radical polymerisation and is liquid at room temperature and normal pressure. The solubility of the dibenzoyl peroxide in these liquids at room temperature is less than 5% by weight. Mixed glycerol-triesters of octanoic acid and decanoic acid, which are commercially available by the brand name of Miglyol® 812 (CAS no. 52622-27-2), are particularly well-suited. Upon mixing with particulate dibenzoyl peroxide, this liquid forms flowable pastes that can be moved particularly well in cartridges with small diameters due to the lubricating effect of the Miglyol® 812. It is feasible just as well to use polar liquids such as water, glycerol, diglycerol, and polyethylene glycol. If these polar liquids are contained in component B and component A is mixed with component B, said polar liquids lead to a somewhat delayed curing of the cement dough formed. Polyethylene glycol 200, polyethylene glycol 400, and polyethylene glycol 600 are conceivable as polyethylene glycol.

Preferably, component B contains hardly any biocompatible polymer powder, such as homo- or co-polymerisation products of acrylic and/or methacrylic esters, styrene, vinyl derivatives or mixtures thereof. Their content preferably is less than 0.1 wt. %, particularly preferably less than 0.01 wt. %, and even more particularly preferably less than 0.001 wt. %.

The weight ratio of dibenzoyl peroxide BI and liquid substance BII is more than or equal to 1:1 and preferably more than or equal to 1:0.8.

Dibenzoyl peroxide BI has a sieved fraction with a grain size of less than or equal to 63 µm. By this means, uniform distribution of the dibenzoyl peroxide is attained when component B and component A are mixed with each other.

For colouring the mixed paste cement dough, pasty component B can have a colour pigment suspended in it that is insoluble in liquid substance BII. In this context, especially aluminium coloir lacquers, such as "color lacquer green", the aluminium colour lacquer of a mixture of food colourant E104 (quinoline yellow) and E132 (indigotine), are conceivable.

Pasty component A can be subjected to a sterilisation, e.g. by means of a sterilising agent. The paste can be sterilised, e.g., using the sterilisation method described in EP 2 59 6812 A1 through the action of β-propiolactone or the derivatives thereof. Paste B can be sterilised either by gamma irradiation, electron irradiation or by treatment with β-propiolactone.

According to the invention, pasty component A is tack-free according to ISO standard 5833 according to the "doctor's finger test". This ensures that the cement dough generated after the mixing of component A and component B is tack-free right away, without any waiting time, and can therefore be applied instantaneously.

The invention also relates to a method for producing a self-curing cement using the two-component polymethacrylate bone cement according to the invention, which comprises mixing pasty component A and pasty component B to form a self-curing cement dough. The two components are preferably mixed at a weight ratio of 96 to 99.9 parts by weight of paste A to 0.1 to 4 parts by weight of paste B.

The mixing process of the two components can be separated in time from the extrusion process. The two components can be mixed, e.g. in a cartridge, such as a plastic cartridge, and the cement dough thus formed can be extruded using an extrusion device. For example, conventional, manually driven extrusion devices that are used with conventional two-component pasty bone cements as well are suitable for this purpose.

After the mixing of paste A and paste component B, a tack-free plastically deformable cement dough is generated immediately, without any waiting time, that self-cures by means of radical polymerisation.

The pasty two-component polymethacrylate bone cement according to the invention is used to particular advantage for the production of a means for the fixation of total articular endoprostheses and revision articular endoprostheses.

Moreover, the pasty two-component polymethacrylate bone cement is used for the production of a means for vertebroplasty, for kyphoplasty, for femoral neck augmentation, and for the production of spacers.

The pasty two-component polymethacrylate bone cement can also be used for the production of local agent release systems. These can take the shape of beads, bean-shaped spherical bodies, rods, tubes, and irregularly shaped bodies.

The invention shall be illustrated in more detail based on the following examples 1-5.

PRODUCTION OF PASTY COMPONENT A OF EXAMPLES 1-5

Pasty component A of examples 1 to 5 was produced by mixing the ingredients specified in Table 1.

TABLE 1

| | Composition of pasty component A | | | | |
|---|---|---|---|---|---|
| | Example 1 | Example 2 | Example 3 | Example 4 | Example 5 |
| Methylmethacrylate | 42.50 g | 42.50 g | 42.50 g | 42.50 g | 42.50 g |
| Polymethylmethacrylate-co-methylacrylate | 30.50 g | 30.50 g | 30.50 g | 30.50 g | 30.50 g |
| Cross-linked polymethyl methacrylate | 15.45 g | 15.45 g | 15.45 g | 15.45 g | 15.45 g |
| Methacrylamide | 0.40 g | 0.40 g | 0.40 g | 0.40 g | 0.40 g |
| 2,5-Di-t-butylhydroquinone | 50 mg | 50 mg | 50 mg | 50 mg | 50 mg |
| N,N-Dimethyl-p-toluidine | 0.35 g | 0.35 g | 0.35 g | 0.35 g | 0.35 g |
| Green lacquer | 5 mg | 5 mg | 5 mg | 5 mg | 5 mg |
| Gentamicin sulfate Activity coefficient AK 580 | — | 1.47 | — | — | — |
| Clindamycin hydrochloride | — | — | 1.50 | — | — |
| Vancomycin hydrochloride | — | — | — | 1.50 | — |
| Trometamol-fosfomycin | — | — | — | — | 1.50 |

Composition of pasty component B:

10.0 g BPO (75%, phlegmatised with 25% by weight water)

4.0 g Mygliol

The components of pasty component B of examples 1-5 were weighed in plastic cans, homogenised by stirring, and then closed in airtight manner with a screw lid. The pasty components B were stored at room temperature in the air-tightly closed plastic cans until use.

The two components A and B were ground together until a colourless creamy-pasty mass was generated.

The substances of pasty components A and B were procured from Sigma-Aldrich with the exception of the soluble poly-methylmethacrylate-co-methylacrylate and the insoluble polymethylmethacrylate, which were made available by polymer manufacturers. The trometamol-fosfomycin was procured from ZaChem S.p.A. Gentamicin sulfate from Fujian Fukang Ltd. (PR China) was used.

Production of Test Bodies:

ISO 5833 requires a flexural strength of 50 MPa, a flexural modulus of 1,800 MPa, and compressive strength of 70 MPa. Test bodies were produced for the test of the mechanical properties of the paste cements of examples 1-5 in accordance with ISO 5833. A total of 40 g paste A were vigorously stirred with 1.40 g of each of the pasty component B of examples 1-5. An immediately tack-free green cement dough that cured by exothermic reaction after just a few minutes was thus produced immediately in all examples. Each cement dough of examples 1-5 was used to produce strip-shaped test bodies sized 75 mm×10 mm×3.3 mm for the test of the flexural strength and flexural modulus in accordance with ISO 5833. In addition, cylindrical test bodies (diameter 6 mm, height 12 mm) were manufactured for the compressive strength test.

After storage of the test bodies at 23° C. and a relative humidity of 50% for a period of 24 hours, the flexural strength, flexural modulus, and compressive strength were determined in accordance with ISO 5833. The results in Table 2 show that the mechanical requirements of ISO 5833 with regard to the flexural strength, flexural modulus, and compressive strength were met by the cements of examples 1-5.

TABLE 2

| Example | Flexural strength [MPa] | Flexural modulus [MPa] | Compressive strength [MPa] |
|---|---|---|---|
| 1 | 65.3 ± 2.6 | 2651 ± 84 | 97.1 ± 3.2 |
| 2 | 62.8 ± 1.6 | 2651 ± 28 | 88.0 ± 2.6 |
| 3 | 64.6 ± 1.3 | 2712 ± 43 | 93.3 ± 3.7 |
| 4 | 62.1 ± 2.5 | 2637 ± 72 | 96.1 ± 3.0 |
| 5 | 63.2 ± 1.4 | 2575 ± 70 | 88.8 ± 1.8 |

EXAMPLES 6-10

Pasty component A and pasty component B were produced in the same manner as in examples 1-5, except that 0.1 wt. % β-propiolactone was added to each pasty component A and pasty component B. Pasty component A and pasty component B were manually mixed with each other 2 weeks after their production and after storage at room temperature using the same mixing ratio as in examples 1-5. Similar to examples 1-5, a green, tack-free cement dough was produced that was plastically deformable for approximately 3 minutes and 30 seconds and then cured by exothermic reaction within approximately 4 minutes.

EXAMPLES 11-15

Pasty component A and pasty component B were produced in the same manner as in examples 6-10, except that 0.1 wt. % propiolactone was added to each pasty component A and pasty component B. Pasty component A and pasty component B were placed in special side-by-site cartridges 2 weeks after their production and after storage at room temperature using the same mixing ratio as in examples 1-5. Subsequently, each of said cartridges was connected to a dispensing tube and to a static mixer arranged therein and then extruded with a manually operable extrusion device. Similar to examples 1-5, a green, immediately tack-free cement dough was produced during extrusion that was plastically deformable for approximately 3 minutes and 30 seconds and then cured by exothermic reaction within approximately 4 minutes.

EXAMPLES 16-20

A mixture of 10.0 g dibenzoyl peroxide (75%, phlegmatised with 25% by weight water) and 4.0 g glycerol was used as pasty component B. The composition of pasty component A was the same as in examples 1-5. Pasty component A and pasty component B were placed in special side-by-site cartridges one day after their production and after storage at room temperature using the same mixing ratio as in examples 1-5. Subsequently, each of said cartridges was connected to a dispensing tube and to a static mixer arranged therein and then extruded with a manually operable extrusion device. Similar to examples 1-5, an immediately tack-free, green cement dough was produced during extrusion that was plastically deformable for approximately 4.5 minutes and then cured by exothermic reaction within approximately 4 minutes.

EXAMPLES 21-25

A mixture of 10.0 g dibenzoyl peroxide (75%, phlegmatised with 25% by weight water) and 4.0 g water was used as pasty component B. The composition of pasty component A was the same as in examples 1-5. Pasty component A and pasty component B were placed in special side-by-site cartridges one day after their production and after storage at room temperature using the same mixing ratio as in examples 1-5. Subsequently, each of said cartridges was connected to a dispensing tube and to a static mixer arranged therein and then extruded with a manually operable extrusion device. Similar to examples 1-5, an immediately tack-free, green cement dough was produced during extrusion that was plastically deformable for approximately 4 to 5 minutes and then cured by exothermic reaction within approximately 4 minutes.

The invention claimed is:
1. Pasty two-component polymethacrylate bone cement comprising a pasty component A, comprising:
AI at least one distillable methacrylate monomer for radical polymerisation;
AII at least one polymer that is soluble in AI;
AIII at least one particulate polymer with a particle size of no more than 500 μm that is not soluble in AI;
AIV at least one radical stabiliser; and
AV at least one accelerator from the group of aromatic amines;
and
a pasty component B, consisting of:
BI dibenzoyl peroxide; and
BII at least one substance that is not subject to radical polymerisation and is liquid at room temperature, whereby the solubility of dibenzoyl peroxide in this substance at room temperature is less than 5.0% by weight; and
optionally at least one color pigment that is insoluble in liquid substance BII; and
whereby the weight fraction of liquid substance BII in the self-curing cement dough thus formed after the mixing of pasty component A with pasty component B is completed is less than 2.0% by weight.
2. Pasty two-component polymethacrylate bone cement according to claim 1, wherein pasty component A contains
AI 20-60 wt. % of the at least one distillable methacrylate monomer for radical polymerisation;
AII 15-45 wt. % of the at least one polymer that is soluble in AI;
AIII 15-45 wt. % of the at least one particulate polymer with a particle size of at most 500 μm that is not soluble in AI.
3. Pasty two-component polymethacrylate bone cement according to claim 1, wherein
the weight ratio of dibenzoyl peroxide BI and liquid substance BII is more than or equal to 1:1.
4. Pasty two-component polymethacrylate bone cement according to claim 1, wherein
the weight ratio of pasty component A and pasty component B is more than or equal to 96 to 4.
5. Pasty two-component polymethacrylate bone cement according to claim 1, wherein
BII is selected from water, glycerol, diglycerol, glycerol-tri-octoate, glycerol-tri-decanoate, polyethylene glycol, sebacinc acid dibutylester, and mixtures thereof.
6. Pasty two-component polymethacrylate bone cement according to claim 1, wherein
BI dibenzoyl peroxide has a sieved fraction with a grain size of less than or equal to 63 μm.
7. Pasty two-component polymethacrylate bone cement according to claim 1, wherein the accelerator AV is selected from the group consisting of N,N-dimethyl-p-toluidine, N,N-bis-hydroxyethyl-p-toluidine, and N,N-dimethyl-p-hydroxyethyl-aniline.
8. Pasty two-component polymethacrylate bone cement according to claim 1, wherein
AI the methacrylate monomer is selected from the group consisting of methylmethacrylate and ethylene glycol dimethacrylate.
9. Pasty two-component polymethacrylate bone cement according to claim 1, wherein
polymer AII is selected from the group of polymethylmethacrylate copolymers.
10. Pasty two-component polymethacrylate bone cement according to claim 9, wherein
polymer AII is selected from the group consisting of polymethylmethacrylate-co-methylacrylate and polymethylmethacrylate-co-styrene.
11. Pasty two-component polymethacrylate bone cement according to claim 1, wherein
AII is selected from the group consisting of cross-linked polymethylmethacrylate and cross-linked polymethylmethacrylate-co-methylacrylate.
12. Pasty two-component polymethacrylate bone cement according to claim 1, wherein
the radical stabiliser AIV is selected from the group consisting of p-benzoquinone, o-benzoquinone, 2,5-di-t-butylhydroquinone, p-hydroquinone and phenothiazine.
13. Pasty two-component polymethacrylate bone cement according to claim 1, wherein pasty component A contains, as excipients, one or substances selected from the group consisting of methacrylate-soluble colourants, methacrylate-insoluble colour pigments, pyrogenic silicon dioxide, and methacrylic amide.
14. Pasty two-component polymethacrylate bone cement according to claim 1, wherein
pasty component A contains one or more pharmaceutical agent(s) selected from the group consisting of antibiotics, hormones, growth factors, and antiphlogistic agents.

15. Pasty two-component polymethacrylate bone cement according to claim 1, wherein
pasty component A contains at least one radiopaquer selected from the group consisting of zirconium dioxide, barium sulfate, tantalum, and biocompatible calcium salts.

16. Pasty two-component polymethacrylate bone cement according to claim 1, wherein
a colour pigment that is insoluble in liquid substance BII is suspended in pasty component B.

17. Method for producing a self-curing bone cement using the two-component polymethacrylate bone cement according to claim 1, comprising mixing pasty component A and pasty component B at a weight ratio of more than or equal to 96 to 4.

18. Method of using the pasty two-component polymethacrylate bone cement according to claim 1 for the production of a means for fixation of total articular endoprostheses and revision articular endoprostheses.

19. Method of using a pasty two-component polymethacrylate bone cement according to claim 1 for the production of a means for vertebroplasty, for kyphoplasty, for femoral neck augmentation, and for the production of spacers.

20. Method of using the pasty two-component polymethacrylate bone cement according to claim 1 for the production of local agent release systems.

21. Pasty two-component polymethacrylate bone cement according to claim 1, wherein liquid substance BII is selected from the group consisting of glycerol, diglycerol, glycerol-tri-octoate, glycerol-tri-decanoate, polyethylene glycol, sebacic acid dibutylester, mixed glycerol-triesters of octanoic acid and decanoic acid, and mixtures thereof.

* * * * *